US012048425B2

(12) United States Patent
Awadu (10) Patent No.: US 12,048,425 B2
(45) Date of Patent: Jul. 30, 2024

(54) FLEXIBLE ENDOSCOPE INSERTION METHOD FOR EXAMINING THE LATERAL WALL OF THE LUMEN OR THE LATERAL SIDE OF THE ORGAN

(71) Applicant: Satoshi Awadu, Nagasaki (JP)

(72) Inventor: Satoshi Awadu, Nagasaki (JP)

( * ) Notice: Subject to any disclaimer, the term of this patent is extended or adjusted under 35 U.S.C. 154(b) by 768 days.

(21) Appl. No.: 16/998,392

(22) Filed: Aug. 20, 2020

(65) Prior Publication Data

US 2022/0054118 A1 Feb. 24, 2022

(51) Int. Cl.
*A61B 1/005* (2006.01)
*A61B 1/233* (2006.01)
(Continued)

(52) U.S. Cl.
CPC ...... *A61B 17/00234* (2013.01); *A61B 1/0051* (2013.01); *A61B 1/233* (2013.01); *A61B 1/24* (2013.01); *A61B 1/2676* (2013.01); *A61B 1/2733* (2013.01); *A61B 1/303* (2013.01); *A61B 1/307* (2013.01); *A61B 18/02* (2013.01); *A61B 18/12* (2013.01); *A61B 18/24* (2013.01); *A61B 2017/0034* (2013.01); *A61B 17/02* (2013.01); *A61B 17/0469* (2013.01); *A61B 17/122* (2013.01); *A61B 17/16* (2013.01); *A61B 17/29* (2013.01); *A61B 17/320016* (2013.01); *A61B 17/320068* (2013.01); *A61B 2017/320082* (2017.08); *A61B 2018/00494* (2013.01); *A61B 2018/00982* (2013.01);
(Continued)

(58) Field of Classification Search
None
See application file for complete search history.

(56) References Cited

U.S. PATENT DOCUMENTS 4,577,621 A * 3/1986 Patel .................. A61B 1/00156
600/114
5,078,743 A * 1/1992 Mikalov ................ A61F 2/203
623/14.11
(Continued)

OTHER PUBLICATIONS

Safiruddin-Koutsourelakis-Vries <Upper airway collapse during drug induced sleep endoscopy> 2014.*
(Continued)

*Primary Examiner* — John P Leubecker
(74) *Attorney, Agent, or Firm* — Renner, Otto, Boisselle & Sklar, LLP (57) ABSTRACT

A flexible endoscope insertion method includes: rotating a hollow organ by changing the body position to semilateral position or lateral position for observing the lateral wall of the lumen; turning the tip of the flexible endoscope to the lateral wall of the lumen by rotating the endoscope in the counter direction of the lumen; and retracting the organ with the endoscope itself by rotating the endoscope in the counter direction of the lumen. In other embodiments, the method includes: rotating a body cavity by changing the body position to the appropriate position for observing the lateral side of the organ; turning the tip of the flexible endoscope to the lateral side of the organ by rotating the endoscope in the direction of the lateral side of the organ; and retracting the organ with the endoscope itself by rotating the endoscope in the direction of the lateral side of the organ.

15 Claims, 8 Drawing Sheets

(51) Int. Cl.
*A61B 1/24* (2006.01)
*A61B 1/267* (2006.01)
*A61B 1/273* (2006.01)
*A61B 1/303* (2006.01)
*A61B 1/307* (2006.01)
*A61B 17/00* (2006.01)
*A61B 18/02* (2006.01)
*A61B 18/12* (2006.01)
*A61B 18/24* (2006.01)
*A61B 17/02* (2006.01)
*A61B 17/04* (2006.01)
*A61B 17/122* (2006.01)
*A61B 17/16* (2006.01)
*A61B 17/29* (2006.01)
*A61B 17/32* (2006.01)
*A61B 18/00* (2006.01)
*A61B 18/14* (2006.01)
*A61M 25/10* (2013.01)

(52) U.S. Cl.
CPC ............ *A61B 2018/00994* (2013.01); *A61B 2018/1422* (2013.01); *A61M 25/10* (2013.01)

(56) References Cited

U.S. PATENT DOCUMENTS

| | | | | |
|---|---|---|---|---|
| 5,599,304 | A * | 2/1997 | Shaari | A61M 1/84 604/173 |
| 5,624,439 | A * | 4/1997 | Edwards | A61B 18/1485 606/41 |
| 5,816,257 | A * | 10/1998 | Chin | A61B 17/00 604/500 |
| 5,842,973 | A * | 12/1998 | Bullard | A61M 16/0418 600/114 |
| 5,855,207 | A * | 1/1999 | Moenning | A61G 7/1057 5/81.1 R |
| 6,053,172 | A * | 4/2000 | Hovda | A61B 18/1482 606/41 |
| 9,561,055 | B1 * | 2/2017 | Karim | A61B 17/7058 |
| 2003/0040681 | A1 * | 2/2003 | Ng | A61B 10/02 600/562 |
| 2003/0220551 | A1 * | 11/2003 | Kimball | A61B 5/412 600/345 |
| 2004/0035429 | A1 * | 2/2004 | Wakabayashi | A61M 16/04 128/207.15 |
| 2004/0127800 | A1 * | 7/2004 | Kimball | A61B 5/14539 600/483 |
| 2006/0063973 | A1 * | 3/2006 | Makower | A61B 17/282 600/114 |
| 2006/0235352 | A1 * | 10/2006 | Dziewas | A61B 1/2736 604/43 |
| 2007/0083225 | A1 * | 4/2007 | Kiser | A61M 29/02 606/192 |
| 2007/0137654 | A1 * | 6/2007 | Paraschac | A61F 5/56 128/848 |
| 2007/0137655 | A1 * | 6/2007 | Paraschac | A61F 5/56 128/848 |
| 2007/0250105 | A1 * | 10/2007 | Ressemann | A61B 17/12136 606/196 |
| 2008/0249359 | A1 * | 10/2008 | Abraham-Fuchs | A61B 5/704 600/117 |
| 2009/0227864 | A1 * | 9/2009 | Sato | A61B 1/041 600/103 |
| 2010/0174366 | A1 * | 7/2010 | Avior | A61F 11/202 623/10 |
| 2010/0331619 | A1 * | 12/2010 | Miyoshi | A61B 1/00177 600/101 |
| 2013/0027531 | A1 * | 1/2013 | Miyoshi | A61B 1/3132 348/E7.085 |
| 2014/0039259 | A1 * | 2/2014 | Okaniwa | A61B 1/005 600/139 |
| 2014/0249464 | A1 * | 9/2014 | Godin | A61F 5/0076 604/8 |
| 2015/0342445 | A1 * | 12/2015 | Jones | A61B 1/00133 600/106 |
| 2017/0119582 | A1 * | 5/2017 | Chan | A61B 1/00183 |
| 2018/0125560 | A1 * | 5/2018 | Saadat | A61B 18/02 |
| 2018/0338806 | A1 * | 11/2018 | Grubbs | A61B 34/30 |
| 2019/0254563 | A1 * | 8/2019 | Nakamitsu | A61B 1/045 |
| 2020/0000316 | A1 * | 1/2020 | Ikeda | A61B 1/0005 |
| 2020/0093353 | A1 * | 3/2020 | Tezuka | A61B 1/00006 |
| 2020/0129046 | A1 * | 4/2020 | Sinay | A61B 1/008 |
| 2020/0138269 | A1 * | 5/2020 | Nishimura | A61B 1/0005 |

OTHER PUBLICATIONS

Awazu et al., "A linear sigmoid colon passage method by left twisting", Awazu Hospital, Nagasaki, Japan, PeerJ PrePrints, Nov. 12, 2013.

Awazu et al., "A linear sigmoid colon passage method in colonoscopy", Awazu Hospital, Nagasaki, Japan, PeerJ PrePrints, Oct. 13, 2014.

Awazu et al., "A method of linear passage through the sigmoid colon in colonoscopy", Gastrointestinal Endoscopy, pp. 702-704, vol. 75, No. 3, 2012.

* cited by examiner

FLEXIBLE ENDOSCOPE INSERTION METHOD FOR EXAMINING THE LATERAL WALL OF THE LUMEN OR THE LATERAL SIDE OF THE ORGAN

TECHNICAL FIELD

The present invention relates to the flexible endoscopic diagnosis and treatment.

BACKGROUND

Malignant tumors of the Eustachian tube, tympanic cavity, mastoid antrum, maxillary sinus, frontal sinus, sphenoidal sinus, ethmoidal sinus, nasolacrimal duct, or lachrymal sac has not been diagnosed systematically, and their prognosis has been poor. Therefore, the establishment of a system for their diagnosis and treatment has been needed.

First, in the patient with carcinogenic risk due to chronic inflammatory disease of the Eustachian tube, tympanic cavity, mastoid antrum, maxillary sinus, frontal sinus, sphenoidal sinus, ethmoidal sinus, nasolacrimal duct, or lachrymal sac, the endoscopic diagnosis has been needed before the stage in which they become detectable by PET-CT or PET-MRI, for example, 5 mm in diameter. Also, tumors of the Eustachian tube, tympanic cavity, mastoid antrum, maxillary sinus, frontal sinus, sphenoidal sinus, ethmoidal sinus, nasolacrimal duct, or lachrymal sac 10 mm in diameter can be detected by using PET-CT or PET-MRI and can be treated by using proton therapy or carbon ion radiotherapy. Therefore, the endoscopic diagnosis of these tumors has been needed.

Transnasal flexible endoscopic observation of the pharyngeal orifice of the Eustachian tube, the Rosenmüller's fossa, or the roof of the nasal cavity, and transoral flexible endoscopic observation of the tonsillar fossa or the oral cavity may be occasionally difficult due to the presence of blind areas. Therefore, the new insertion method has been needed.

Tumorectomy for the pathological diagnosis in the Eustachian tube, tympanic cavity, mastoid antrum, maxillary sinus, frontal sinus, sphenoidal sinus, ethmoidal sinus, nasolacrimal duct, or lachrymal sac, branchial fistulectomy for the treatment of second branchial cleft fistula, transpalatal repair of basal skull base herniation for the treatment of persistent craniopharyngeal canal, transcatheter arterial embolization for the treatment of posterior epistaxis, the surgical treatment of skull base cerebrospinal fluid leak, palatal obturator insertion for the treatment of oronasal fistula, mastoidectomy for the treatment of mastoiditis, transcanalicular balloon catheter dilation of the nasolacrimal duct for the treatment of nasolacrimal duct obstruction, transcanalicular nasolacrimal duct recanalization for the treatment of nasolacrimal duct obstruction, transcanalicular nasolacrimal silicone stent intubation for the treatment of nasolacrimal duct obstruction have been invasive. Therefore, the new flexible endoscopic procedure has been needed.

Transnasal balloon catheter insertion into the Eustachian tube for the treatment of Eustachian tube dysfunction, transnasal laser catheter insertion into the Eustachian tube for the treatment of Eustachian tube dysfunction, transnasal endoscopic injection into the torus tubarius for the treatment of patulous Eustachian tube, surgical transtympanic catheter insertion into the Eustachian tube for the treatment of patulous Eustachian tube have occasionally been difficult. Therefore, the new flexible endoscopic procedure has been needed.

The nasopharynx or nasal cavity have not been examined in transoral flexible gastroscopy, and when a transnasal flexible endoscope cannot be inserted due to the obstruction and said flexible endoscope is transorally inserted, the obstructive disorder has not been diagnosed. Therefore, the new insertion method has been needed.

Flexible endoscopic diagnosis and treatment of the lateral wall of the hypopharynx, larynx, trachea, bronchus, bile duct, pancreatic duct, duodenum, stomach, esophagus, urethra, bladder, ureter, renal pelvis, vagina, and uterus has been difficult. Therefore, the new insertion method has been needed.

Flexible endoscopic retraction method for securing the broader operative field has been needed in natural orifice transluminal endoscopic surgery or single-incision flexible endoscopic surgery.

SUMMARY OF THE INVENTION

In the present invention, the diagnosis and treatment of the lateral wall of the lumen can be performed by changing the body position, rotating the flexible endoscope in the counter direction of the lumen, and retracting the organ with the flexible endoscope itself. Also, the diagnosis and treatment of the lateral side of the organ can be performed by changing the body position, rotating the flexible endoscope in the direction of the lateral side of the organ, and retracting the organ with the flexible endoscope itself.

Problems to be Resolved by the Invention

To provide novel methods for the diagnosis and treatment by using the endoscope.

Means of Solving the Problems

In accordance with an aspect of the present disclosure, a flexible endoscope insertion method comprises: (a) rotating a hollow organ by 45 to 90 degrees by changing the body position to the semilateral position or the lateral position for observing the lateral wall of the lumen, wherein the previous body position was the supine, semi-recumbent, sitting, lithotripsy, or prone position; (b) turning the tip of the flexible endoscope to the lateral wall of the lumen by rotating the flexible endoscope in the counter direction of the lumen; and (c) retracting the organ with the flexible endoscope itself by rotating the flexible endoscope in the counter direction of the lumen for securing the visual field.

In some embodiments, (b) comprises: inserting the flexible endoscope into a next lumen while rotating the flexible endoscope in the direction of the lumen; turning the tip of the flexible endoscope to the lateral wall of the next lumen by rotating the flexible endoscope in the counter direction of the lumen; and examining the lateral wall of the next lumen. In some embodiments, the flexible endoscope insertion method comprises the steps of: placing the patient in the left lateral position; inserting the flexible endoscope into the nasopharynx while rotating the flexible endoscope to the right; turning the tip of the flexible endoscope to the right lateral wall of the nasopharynx by rotating the flexible endoscope to the left; and examining the pharyngeal orifice of the right Eustachian tube.

In some embodiments, (b) comprises turning the tip of the flexible endoscope by rotating the flexible endoscope by 360 degrees in the counter direction of the lumen, wherein more larger looping of the flexible endoscope is made in the lumen. In some embodiments, the pharyngeal orifice of the Eustachian tube can be observed from a front by rotating the flexible endoscope by 360 degrees in the counter direction of the lumen in the oropharyngeo-nasopharyngeal cavity, and wherein more larger looping of the flexible endoscope is made in the oropharyngeo-nasopharyngeal cavity. In some embodiments, the flexible endoscope insertion method comprises the steps of: placing the patient in the left lateral position; inserting the flexible endoscope into the oropharynx; turning the tip of the flexible endoscope to the left by rotating or twisting the flexible endoscope to the left (counterclockwise) by 90 degrees; further more turning the tip of the flexible endoscope to the left by rotating the flexible endoscope to the left (counterclockwise) by 180 degrees; inserting the flexible endoscope into the nasopharynx while rotating the flexible endoscope to the left by 90 degrees; and directing the tip of the flexible endoscope to the right lateral wall of the nasopharynx; examining the pharyngeal orifice of the right Eustachian tube.

In some embodiments, the flexible endoscope is transorally inserted into the nasopharnx, the Rosenmüller's fossa, the persistent craniopharyngeal canal, the Eustachian tube, the tympanic cavity, the mastoid antrum, the nasal cavity, the maxillary sinus, the frontal sinus, the sphenoidal sinus, the ethmoidal sinus, the nasolacrimal duct, or the lachrymal sac. In some embodiments, the flexible endoscope insertion method comprises the steps of: placing the patient in the left lateral position; inserting the flexible endoscope into the nasopharynx while rotating or twisting the flexible endoscope to the right (clockwise); and inserting the flexible endoscope into the nasal cavity. In some embodiments, the flexible endoscope insertion method comprises the steps of: placing the patient in the right lateral position; inserting the flexible endoscope into the nasopharynx while rotating the flexible endoscope to the left (counterclockwise); and inserting the flexible endoscope into the nasal cavity.

In some embodiments, the tonsillar fossa can be observed from a front by medially retracting the tongue with the flexible endoscope itself. In some embodiments, the flexible endoscope insertion method comprises the steps of: placing the patient in the left lateral position; inserting the flexible endoscope through the mouth into the oropharynx; rotating the flexible endoscope to the right so as to be observed the palatine uvula in the direction of 12 o'clock for positioning the flexible endoscope on the lateral side of the tongue; gradually rotating the flexible endoscope to the left while maintaining a slight distance between the flexible endoscope and the right posterior palatine arch for medially retracting the tongue with the flexible endoscope itself; inserting the flexible endoscope into the right tonsillar fossa by slightly pushing the flexible endoscope; and examining the right tonsillar fossa.

In some embodiments, the lateral palatine region, the maxillary linguogingival region and the incisive papilla region can be observed from a front by rotating the flexible endoscope in the counter direction of the lumen in the oral cavity, wherein the flexible endoscope looping is made in the oral cavity.

In some embodiments, the flexible endoscope is inserted into the hypopharynx, larynx, trachea, bronchus, bile duct, pancreatic duct, duodenum, stomach, esophagus, urethra, bladder, ureter, renal pelvis, vagina, uterus, or fallopian tube.

In some embodiments, a device used in the method comprises: a tube with a nozzle that can spray over an area of 15-25 mm in diameter from a distance of 15-20 mm, an endoscope with a nozzle that can spray over an area of 15-25 mm in diameter from a distance of 15-20 mm, a nasal plug 7-12 mm in diameter, a flexible endoscope, biopsy forceps, a high-frequency electric knife, a laser catheter, a balloon catheter, a drill, a high speed drill, an endoscopic clip, a tube for the treatment of second branchial cleft fistula, wherein the drug is infused through the internal opening of the second branchial cleft fistula that opens in the tonsillar region, a plug for closing persistent craniopharyngeal canal, a plug for closing cerebrospinal fluid fistula in the treatment of skull base cerebrospinal fluid leak, a plug for closing oronasal fistula, an indwelling drainage catheter for the treatment of mastoiditis, an indwelling drainage catheter for the treatment of sinusitis, a balloon catheter which is inserted through the nasolacrimal duct ostium for the treatment of nasolacrimal duct obstruction, a probe which is inserted through the nasolacrimal duct ostium for the treatment of nasolacrimal duct obstruction, a silicone stent or metallic stent which is inserted through the nasolacrimal duct ostium for the a treatment of nasolacrimal duct obstruction, a balloon catheter and laser catheter for the treatment of Eustachian tube dysfunction, an indwelling catheter for the treatment of Eustachian tube dysfunction, an injection needle for injecting into the torus tubarius in the treatment of patulous Eustachian tube, a catheter for the treatment of patulous Eustachian tube, and a flexible endoscope made of an anti-slip material for retracting the organ.

In accordance with another aspect of the present disclosure, a flexible endoscope insertion method, comprises: (a) rotating a body cavity by 0 to 90 degrees by changing the body position to the appropriate position for observing the lateral side of the organ, wherein the previous body position was the arbitrary body position; (b) turning the tip of the flexible endoscope to the lateral side of the organ by rotating the flexible endoscope in the direction of the lateral side of the organ; and (c) retracting the organ with the flexible endoscope itself by rotating the flexible endoscope in the direction of the lateral side of the organ for securing the visual field.

In some embodiments, (b) and (c) comprise: turning the tip of the flexible endoscope to the lateral side of the organ by rotating the flexible endoscope in the direction of the lateral side of the organ while retracting the organ with the flexible endoscope itself by rotating the flexible endoscope in the direction of the lateral side of the organ for securing the visual field. In some embodiments, the lateral side of the organ can be observed from a front by retracting the organ with the flexible endoscope itself in natural orifice transluminal endoscopic surgery or single-incision flexible endoscopic surgery.

In some embodiments, a device used in the method comprises: a flexible endoscope, biopsy forceps, a high-frequency electric knife, a high-frequency electric hook, a retractor, a grasping forceps, a dissecting forceps, an ultrasonic dissector, a water jet dissector, a bulldog clamp forceps, an endoscopic clip, a scissor, a suture forceps, a laser catheter, a balloon catheter, a drill, a high speed drill, a flexible endoscope made of an anti-slip material for retracting the organ, a port wherein the sliding tube for colonoscopy is shortened to about a few centimeters and the port is placed in the body wall and the flexible endoscope is inserted through the port into the body cavity, a cryoprobe, and a radiofrequency probe.

Effects of the Invention

According to the present invention, the advanced flexible endoscopic diagnosis and treatment can be performed.

DETAILED DESCRIPTION

In the present invention, flexible gastroscope, flexible bronchoscope, flexible laryngoscope, flexible nasopharyngoscope, flexible enteroscope, flexible cholangioscope, flexible pancreatoscope, flexible cystoscope, flexible ureteroscope, flexible hysteroscope, and flexible endoscope (FIG. 12) for natural orifice transluminal endoscopic surgery can be used, but are not restricted to them.

The present invention includes the operation of retracting organs that interrupt the visual field. Organs to be retracted include the tongue, soft palate, torus tubarius, esophagus, stomach, duodenum, small intestine, large intestine, liver, gallbladder, bile duct, pancreas, spleen, adrenal gland, kidney, renal pelvis, ureter, bladder, deferent duct, seminal vesicle, prostate, uterus, vagina, ovary, fallopian tube, lung, trachea, bronchus, thymus, atrium, ventricle, diaphragm, abdominal rectus muscle, abdominal external oblique muscle, abdominal internal oblique muscle, abdominal transverse muscle, greater omentum, mesenterium, artery, vein, nerve, lymph node, and fat but are not restricted to them.

In the present invention, the thickness of the flexible endoscope inserted into the oropharynx, nasopharynx, nasal cavity, Eustachian tube, tympanic cavity, mastoid antrum, maxillary sinus, frontal sinus, sphenoidal sinus, ethmoidal sinus, nasolacrimal duct, and lachrymal sac is preferably 0.5 mm or greater, and more preferably 2.5 mm or greater, and even more preferably 3 mm or greater in minimum diameter, and preferably 15 mm or less, and more preferably 10 mm or less, and even more preferably 6 mm or less in maximum diameter. And it is desirable to use an elastic flexible endoscope about 5 mm in diameter for retracting organs which is surrounded by the cartilage such as the Rosenmüller's fossa or nasal concha, and it is desirable to use a thin flexible endoscope about 3 mm in diameter for examining the narrow site which is surrounded by the bone or the ligament.

In the present invention, flexible endoscopes are preferably equipped with a nozzle for spraying the anesthetic. The minimum spraying distance is preferably 15 mm or more, more preferably 16 mm or more, and even more preferably 17 mm or more, and the maximum spraying distance is preferably 20 mm or less, more preferably 19 mm or less, and even more preferably 18 mm or less. The area sprayed with the anesthetic is preferably 15 mm or more, more preferably 17 mm or more, and even more preferably 19 mm or more in minimum diameter and preferably 25 mm or less, more preferably 23 mm or less, and even more preferably 21 mm or less in maximum diameter.

Spraying angle that can spray over an area of 15-25 mm in diameter from a distance of 15-20 mm is most preferably. To make this possible, the minimum spraying angle is preferably 40 degrees or more, more preferably 50 degrees or more, and even more preferably 55 degrees or more, the maximum spraying angle is preferably 75 degrees or less, more preferably 70 degrees or less, and even more preferably 65 degrees or less.

In the present invention, malignant tumors of the Eustachian tube, tympanic cavity, mastoid antrum, maxillary sinus, frontal sinus, sphenoidal sinus, ethmoidal sinus, nasolacrimal duct, or lachrymal sac can be systemically diagnosed and treated.

First, in the patient with carcinogenic risk due to chronic inflammatory disease of the Eustachian tube, tympanic cavity, mastoid antrum, maxillary sinus, frontal sinus, sphenoidal sinus, ethmoidal sinus, nasolacrimal duct, or lachrymal sac, early diagnosis of these tumors can be performed before the stage in which they become detectable by PET-CT or PET-MRI, for example, 5 mm in diameter.

Also, tumors of the Eustachian tube, tympanic cavity, mastoid antrum, maxillary sinus, frontal sinus, sphenoidal sinus, ethmoidal sinus, nasolacrimal duct, or lachrymal sac 10 mm in diameter, which is detected by using PET-CT or PET-MRI, can be diagnosed by using the transorally inserted flexible endoscope and can be treated by using proton therapy or carbon ion radiotherapy.

Figure 1:
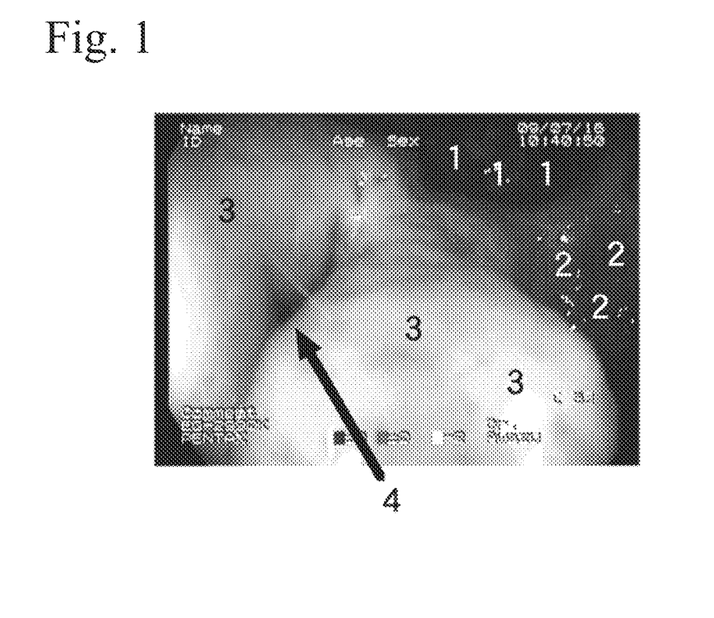
FIG. 1 is a frontal view of the pharyngeal orifice of the right Eustachian tube in the nasopharynx.
Figure 2:
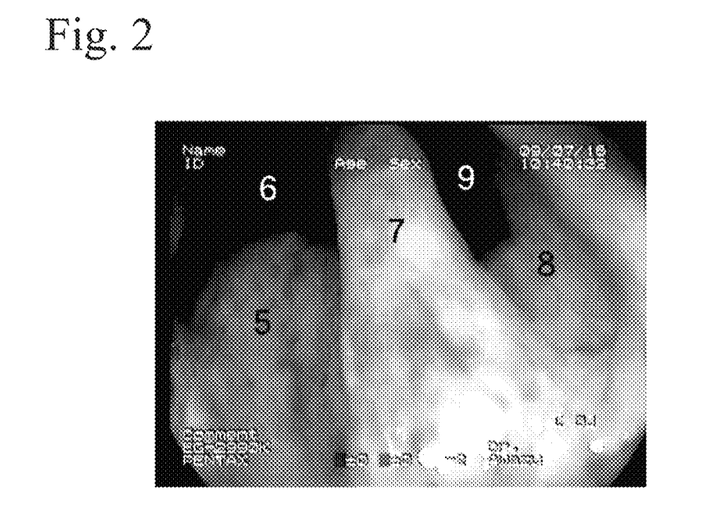
FIG. 2 is a frontal view of the roof of the nasal cavity.
Figure 3:
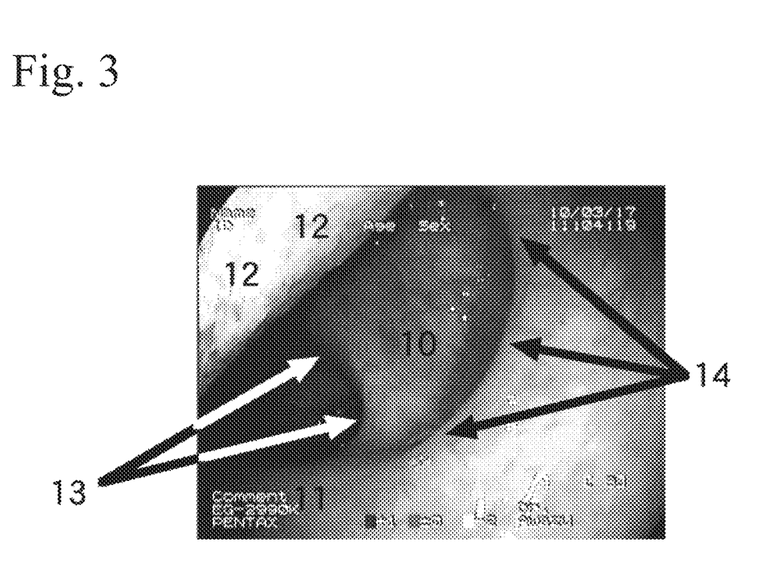
FIG. 3 is a frontal view of the right tonsillar fossa.

In the present invention, the endoscopic observation of the conventionally unexamined areas (such as the pharyngeal orifice of the Eustachian tube (FIG. 1), the Rosenmüller's fossa, the roof of the nasal cavity (FIG. 2), the tonsillar fossa (FIG. 3), or the oral cavity) can be performed by using the transorally inserted flexible endoscope. And images are vertically and horizontally reversed, for example, the right nasal cavity is observed in the left of the screen and the roof of the nasal cavity is observed from the front (FIG. 2), but this poses no problem.

Figure 4A:
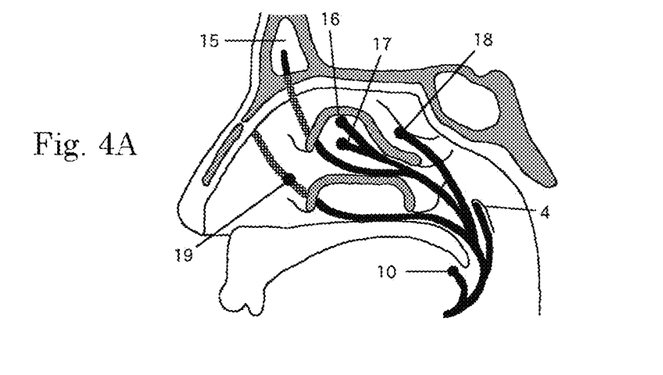
FIGS. 4A, 4B, and 4C are systematic diagrams showing insertion routes of the flexible endoscope.
Figure 4B:
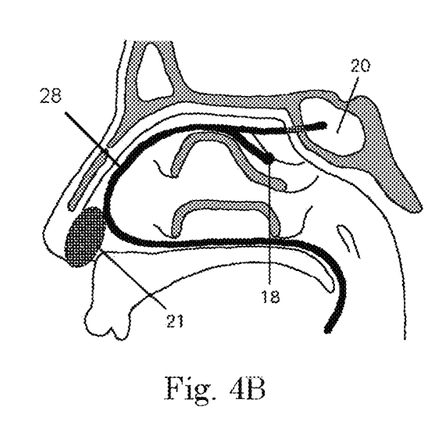
Figure 4C:
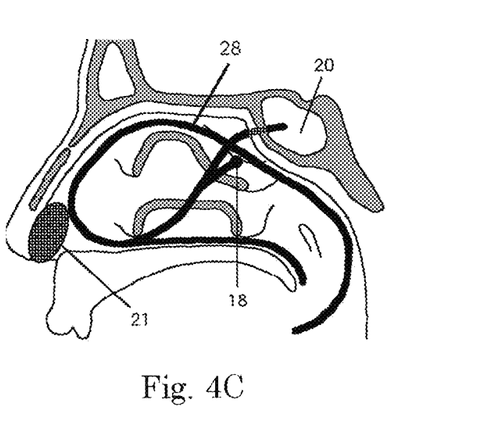

In the present invention, the Eustachian tube, aditus to mastoid antrum, maxillary sinus ostium, frontal sinus ostium, sphenoidal sinus ostium, ethmoidal sinus ostium, or nasolacrimal duct ostium can be dilated by using the balloon catheter, the high speed drill, or the laser catheter for securing the route of insertion (insertion route is shown in FIGS. 4(*a*), 4(*b*), and 4(*c*)), because these portions can be observed from the front. On the other hand, the dilation of these portions has not been performed in conventional endoscopic insertion method.

In the present invention, flexible endoscopic diagnosis can be performed in the Eustachian tube, tympanic cavity, mastoid antrum, maxillary sinus, frontal sinus, sphenoidal sinus, ethmoidal sinus, nasolacrimal duct, or lachrymal sac. Therefore, tumorectomy for the pathological diagnosis in these portions can be escaped.

In the present invention, the injecting tube can be readily inserted through the internal opening of second branchial cleft fistula around the tonsillar fossa by using the transorally inserted flexible endoscope for the treatment of second branchial cleft fistula (endoscopic transoral chemocauterization of second branchial cleft fistula), because the internal opening of second branchial cleft fistula can be observed from the front by the transorally inserted flexible endoscope. On the other hand, branchial fistulectomy has been performed in the conventional treatment.

In the present invention, a plug can be readily placed in the carniopharygeal canal by using the transorally inserted flexible endoscope for the treatment of persistent craniopharyngeal canal (endoscopic transoral transpharyngeal plug closure of craniopharyngeal canal), because the nasopharyngeal orifice of the carniopharyngeal canal can be observed from the front by the transorally inserted flexible endoscope. On the other hand, transpalatal repair of basal skull base herniation has been performed in the conventional treatment.

In the present invention, a hemostatic procedure can be readily performed from the back by using the transorally inserted flexible endoscope for the treatment of posterior epistaxis which cannot be treated by using the transnasally inserted flexible endoscope (endoscopic transoral transpharyngeal hemostatic procedure for epistaxis), because the field of procedure can be brodened. On the other hand, transcatheter arterial embolization has been performed in the conventional treatment.

In the present invention, a plug can be readily placed by using the transorally inserted flexible endoscope for the treatment of skull base cerebrospinal fluid leak (endoscopic transoral transpharyngeal plug closure of skull base cerebrospinal fluid leak). On the other hand, surgery has been performed in the conventional treatment.

In the present invention, a plug can be readily placed by using the transorally and transpharyngeally inserted flexible endoscope for the treatment of oronasal fistula which is a complication of cleft palate surgery (endoscopic transoral transpharyngeal plug closure of the oronasal fistula), because the orifice of the oronasal fistula can be observed from the front by the transorally and transpharyngeally inserted flexible endoscope. On the other hand, conventionally used palatal obturator has occasionally induced dental caries and gingivitis and accidentally been swallowed.

In the present invention, the balloon catheter, the laser catheter and the drainage catheter can be readily inserted through the Eustachian tube into the mastoid antrum by using the transorally inserted flexible endoscope for the treatment of mastoiditis (endoscopic transoral transpharyngeal mastoid drainage), because the pharyngeal orifice of the Eustachian tube can be observed from the front by the transorally inserted flexible endoscope. On the other hand, mastoidectomy has been performed in the conventional treatment.

In the present invention, the cost can be reduced by using the transorally inserted flexible endoscope and balloon catheter for the treatment of sinusitis (endoscopic transoral transpharyngeal balloon sinus ostial dilation). On the other hand, the high cost is required due to the use of special devices (a special balloon catheter) in conventional balloon sinuplasty.

In the present invention, the balloon catheter can be readily inserted through the nasolacrimal duct ostium by using the transorally inserted flexible endoscope for the treatment of nasolacrimal duct obstruction (endoscopic transoral transpharyngeal balloon catheter dilation of the nasolacrimal duct), because the nasolacrimal duct ostium can be observed from the front by the transorally inserted flexible endoscope. On the other hand, there has been the risk of damaging the lachrymal punctum and the unsuccessful catheter insertion through the small lachrymal punctum in conventional transcanalicular balloon catheter dilation of nasolacrimal duct obstruction.

In the present invention, the probe can be readily inserted through the nasolacrimal duct ostium by using the transorally inserted flexible endoscope for the treatment of nasolacrimal duct obstruction (endoscopic transoral transpharyngeal nasolacrimal duct recanalization), because the nasolacrimal duct ostium can be observed from the front by the transorally inserted flexible endoscope. On the other hand, there has been the risk of damaging the lachrymal punctum and the unsuccessful catheter insertion through the small lachrymal punctum in conventional transcanalicular nasolacrimal duct recanalization.

Figure 6A:
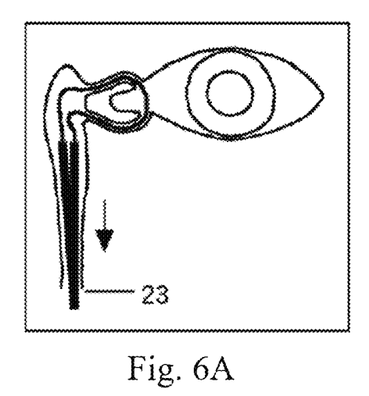
FIG. 6A is an image showing the silicone stent intubation through the lachrymal punctum.
Figure 6B:
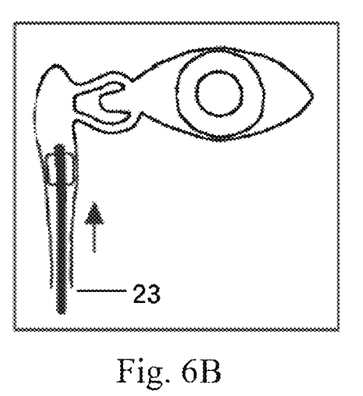
FIG. 6B is an image showing the silicone stent intubation through the nasolacrimal duct ostium.

In the present invention, the silicone stent can be readily inserted through the nasolacrimal duct ostium by using the transorally inserted flexible endoscope for the treatment of nasolacrimal duct obstruction (endoscopic transoral transpharyngeal nasolacrimal silicone stent intubation) (FIG. 6(b)), because the nasolacrimal duct ostium can be observed from the front by the transorally inserted flexible endoscope. On the other hand, there has been the risk of damaging the lachrymal punctum and the unsuccessful stent intubation through the small lachrymal punctum and the occurrence of a foreign body feeling in conventional transcanalicular nasolacrimal silicone stent intubation (FIG. 6(a)).

In the present invention, the metallic stent can be readily inserted through the nasolacrimal duct ostium by using the transorally inserted flexible endoscope for the treatment of nasolacrimal duct obstruction (endoscopic transoral transpharyngeal nasolacrimal metallic stent placement).

In the present invention, the balloon catheter can be readily inserted into of the Eustachian tube by using the transorally inserted flexible endoscope for the treatment of Eustachian tube dysfunction (endoscopic transoral transpharyngeal balloon Eustachian tuboplasty), because the pharyngeal orifice of the Eustachian tube can be observed from the front by the transorally inserted flexible endoscope. On the other hand, transnasal balloon catheter insertion has been performed in the conventional treatment.

Also, the laser catheter can be readily inserted into the Eustachian tube by using the transorally inserted flexible endoscope for the treatment of Eustachian tube dysfunction (endoscopic transoral transpharyngeal laser Eustachian tuboplasty), because the pharyngeal orifice of the Eustachian tube can be observed from the front by the transorally inserted flexible endoscope. On the other hand, transnasal laser catheter insertion has been performed in the conventional treatment.

In the present invention, injection into the torus tubarius can be readily performed by using the transorally inserted flexible endoscope for the treatment of patulous Eustachian tube (transoral endoscopic transoral injection into the torus tubarius), because the torus tubarius can be observed from the front by the transorally inserted flexible endoscope. On the other hand, transnasal endoscopic injection into the torus tubarius has been performed in the conventional treatment.

Figure 5A:
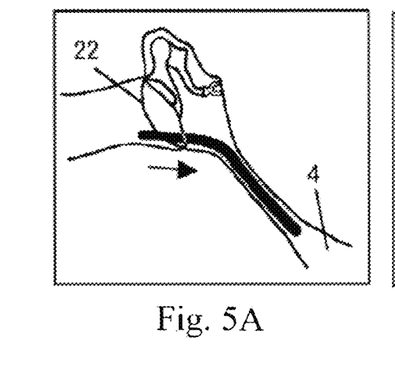
FIG. 5A is an image showing transtympanic catheter insertion into the Eustachian tube.
Figure 5B:
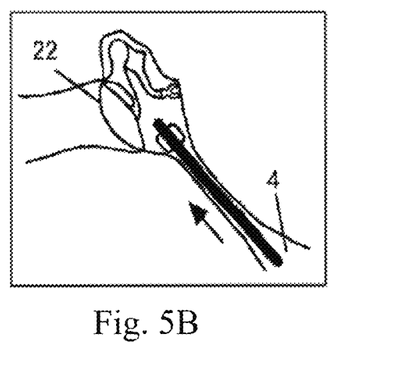
FIG. 5B is an image showing endoscopic transoral transpharyngeal catheter insertion into the Eustachian tube.

In the present invention, the catheter can be readily inserted into the Eustachian tube by using the transorally inserted flexible endoscope for the treatment of patulous Eustachian tube (endoscopic transoral transpharyngeal catheter insertion) (FIG. 5(b)), because the pharyngeal orifice of the Eustachian tube can be observed from the front by the transorally inserted flexible endoscope. On the other hand, surgical transtympanic catheter insertion has been performed in the conventional treatment (FIG. 5(a)).

In the present invention, routine check of the nasopharynx or nasal cavity can be performed in transoral flexible gastroscopy. On the other hand, the nasopharynx or nasal cavity have not been examined in conventional transoral flexible gastroscopy.

In the present invention, the obstructive disorder which prevents the transnasal flexible endoscope insertion can be diagnosed by using the transorally inserted flexible endoscope. On the other hand, when the transnasal flexible endoscope cannot be inserted, the obstructive disorder of the nasopharynx or nasal cavity has not been diagnosed in conventional transnasal flexible endoscopy.

In the present invention, the lateral wall of the hollow organs (hypopharynx, larynx, trachea, bronchus, bile duct, pancreatic duct, duodenum, stomach, esophagus, urethra, bladder, ureter, renal pelvis, vagina, uterus) can be observed from the front, because the hollow organs are rotated in relative terms by changing the body position to the semilateral position or the lateral position. On the other hand, the lateral wall of the hollow organs cannot be observed from the front in the sitting, semi-recumbent, supine, lithotomy, or prone position in conventional flexible endoscopy.

In the present invention, the endoscope insertion into branches which open in the lateral wall of the hollow organs (bronchus, pancreatic duct, bile duct), the endoscope insertion into the fallopian tube and the ureteral access sheath insertion can be readily performed, because the hollow organs are rotated in relative terms by changing the body position to the semilateral position or the lateral position. On the other hand, the endoscope insertion into branches which open in the lateral wall of the hollow organs, the endoscope insertion into the fallopian tube and the ureteral access sheath insertion cannot be occasionally performed in the sitting, semi-recumbent, supine, lithotomy, or prone position in conventional flexible endoscopy.

In the present invention, the retraction of the organs can be readily performed in a narrow space in which retractors or grasping forceps cannot be used in natural orifice transluminal endoscopic surgery (flexible endoscopic organ retraction method in natural orifice transluminal endoscopic surgery), because the organs are retracted with the flexible endoscope itself.

In the present invention, the retraction of the organs can be readily performed in a narrow space in which retractors or grasping forceps cannot be used in single-incision flexible endoscopic surgery (flexible endoscopic organ retraction method in single-incision flexible endoscopic surgery), because the organs are retracted with the flexible endoscope itself.

In the present invention, the flexible endoscopic tongue retraction method was devised for securing the broader operative field in the tonsillar fossa. This method reproduces the surgical retraction procedure with the left hand during laparotomy, and this method is applied to flexible endoscopic surgery for securing the broader operative field.

The flexible colonoscope insertion method invented by the applicant can be referred to paper published in the Gastrointestinal Endoscopy and the 2 unpublished papers posted on the preprint server.

Points of the flexible colonoscope insertion method are as follows.

1) The patient should be placed in the body position in which the entry site is highest and the exit site is lowest (left semiprone position for the sigmoid colon).
2) The flexed flexible colonoscope should be straightened by rotating the flexible colonoscope by 180 degrees or more (in the sigmoid colon, the flexed flexible colonoscope can be straightened by rotating the flexible colonoscope to the left by 180 degrees or more in the left semiprone position).
3) The flexure of the flexible colonoscope should be prevented by applying a torque and pressing the flexible colonoscope against the fixed organ (in the sigmoid colon, the flexure of the flexible colonoscope can be prevented by applying a torque to the left and pressing the flexible colonoscope against the retroperitoneum in the left semiprone position).

The applicant devised the present invention based on the above flexible colonoscope insertion method. The applied points are as follows.

1) Rotating of the hollow organ in relative terms by changing the body position to the semilateral or the lateral position for observing the lateral wall of the lumen.
2) Retracting the organ with the flexible endoscope itself by rotating the flexible endoscope in the counter direction of the lumen for securing the visual field (laterally retracting the torus tubarius, and medially retracting the tongue).
3) Making more larger looping of the flexible endoscope by rotating the flexible endoscope by 360 degrees in the counter direction of the lumen for directing the tip of the flexible endoscope to the pharyngeal orifice of the Eustachian tube.

In the following section, specific examples of implementation are described, but the present invention is not restricted by these examples, and substitutions and improvements usually made by those skilled in the art are included in the invention.

Example 1

Flexible endoscope insertion method into the nasopharynx and the nasal cavity: lidocaine viscous 2% is implemented by several times by 1 ml at 1-minute intervals and the patient swallow it, and a sedative drug is administered. The patient is placed in the left lateral position. The gastroscope is inserted through the mouth, and the esophagus, stomach, duodenum, and hypopharynx are examined, and when the tip of the gastroscope has reached the oropharynx, the gastroscope is inserted into the nasopharynx by gradually rotating the gastroscope to the right and simultaneously gradually applying an upward angle while maintaining a slight distance between the gastroscope and the posterior pharyngeal wall and slightly pushing the gastroscope, and the nasopharynx is examined.

Also, when a beginner performs this operation, the gastroscope may be inserted into the nasopharynx by rotating the gastroscope to the right so as to be observed the palatine uvula in the direction of 3 o'clock, and further rotating the gastroscope to the right while applying an upward angle, and slightly pushing the gastroscope.

When the sedative drug is not effective, since muscles of the nasopharynx are contracted, the examination of the nasopharynx is difficult.

Here, the anesthetic is sprayed over an area of 15-25 mm in diameter from a distance of 15-20 mm by using a tube projected from the gastroscope. The gastroscope is inserted into the pharyngonasal junction by pushing the gastroscope, and the pharyngonasal junction is examined.

Because the pharyngonasal junction is hard, the gastroscope cannot be occasionally inserted into the pharyngonasal junction. At this time, if the gastroscope is continued to be pushed without rotating the gastroscope, the gastroscope may suddenly advance and stimulate the pharyngonasal junction. Therefore, the gastroscope should be advanced while rotating to the left or right. Also, if the gastroscope is advanced to a dead end in the pharyngonasal junction, rotation of the gastroscope becomes difficult and the visual field is narrowed. At this time, if the gastroscope is forced to be rotated, the gastroscope may stimulate the pharyngonasal junction. Therefore, the gastroscope should not be advanced to a dead end in the pharyngonasal junction.

Here, the anesthetic is sprayed over an area of 15-25 mm in diameter from a distance of 15-20 mm by using a tube projected from the gastroscope. The gastroscope is inserted into the nasal cavity by pushing the gastroscope, and the nasal cavity is examined.

Example 2

Figure 8:
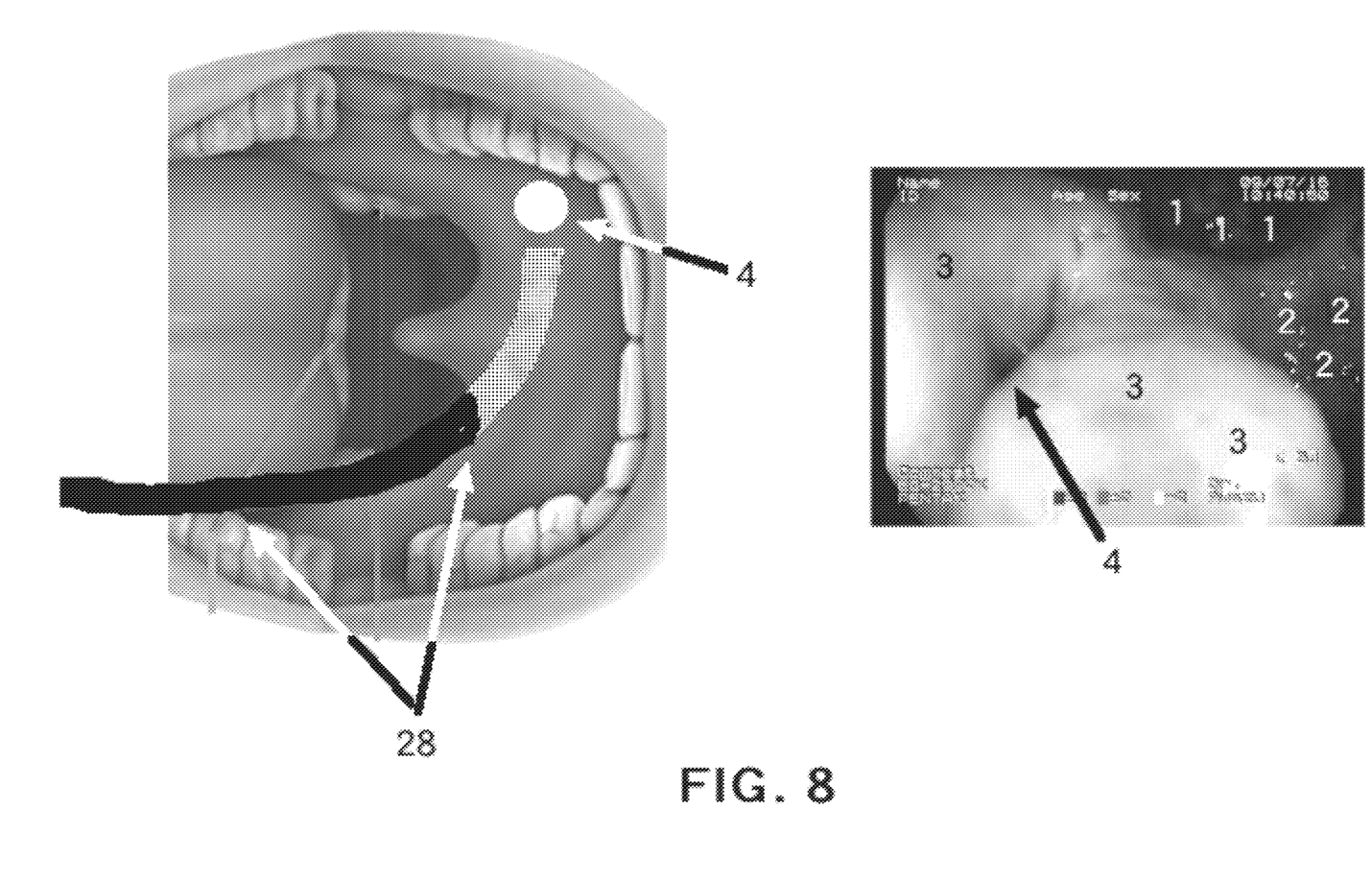
FIG. 8 is an image showing turning the tip of the flexible endoscope to the pharyngeal orifice of the right Eustachian tube.

Flexible endoscope insertion method into the pharyngeal orifice of the right Eustachian tube (FIG. 8): the patient is placed in the left lateral position. The gastroscope is inserted through the mouth into the oropharynx, and the gastroscope is inserted into the nasopharynx by gradually rotating the gastroscope to the right and simultaneously gradually applying an upward angle while maintaining a slight distance between the gastroscope and the posterior pharyngeal wall and slightly pushing the gastroscope, and the tip of the gastroscope is turned to the pharyngeal orifice of the right Eustachian tube by rotating the gastroscope to the left, and the pharyngeal orifice of the right Eustachian tube is examined.

Example 3

Flexible endoscope insertion method into the pharyngeal orifice of the right Eustachian tube by making the more larger looping of the endoscope: the patient is placed in the left lateral position. The gastroscope is inserted through the mouth into the oropharynx, and the tip of the gastroscope is turned to the left by rotating the gastroscope to the left by 90 degrees, and the tip of the gastroscope is turned furthermore to the left by rotating the gastroscope to the left by 180 degrees, and the gastroscope is inserted into the nasopharynx while rotating the gastroscope to the left by 90 degrees, and the tip of the gastroscope is directed to the right lateral wall of the nasopharynx, and the pharyngeal orifice of the right Eustachian tube is examined.

Also, when a beginner performs this operation, the gastroscope may be rotated to the left in the oropharynx so as to be observed the palatine uvula in the direction of 6 o'clock, and the gastroscope is applied a downward angle, and the gastroscope is inserted while further rotating the gastroscope to the left.

Example 4

Flexible endoscope insertion method into the right Rosenmüller's fossa (FIG. 11): the patient is placed in the left semilateral position. The gastroscope 28 is inserted through the mouth into the oropharynx, and the gastroscope is inserted into the nasopharynx by gradually rotating the gastroscope to the right and simultaneously gradually applying an upward angle while maintaining a slight distance between the gastroscope and the posterior pharyngeal wall and slightly pushing the gastroscope. In the nasopharynx, the tip of the gastroscope is turned to the right Rosenmüller's fossa ostium medial to the pharyngeal orifice of the right Eustachian tube by rotating the gastroscope to the left, and the gastroscope is inserted into the right Rosenmüller's fossa 34 while laterally retracting the right torus tubarius 3 with the gastroscope itself, and the right Rosenmüller's fossa is examined.

Figure 11:
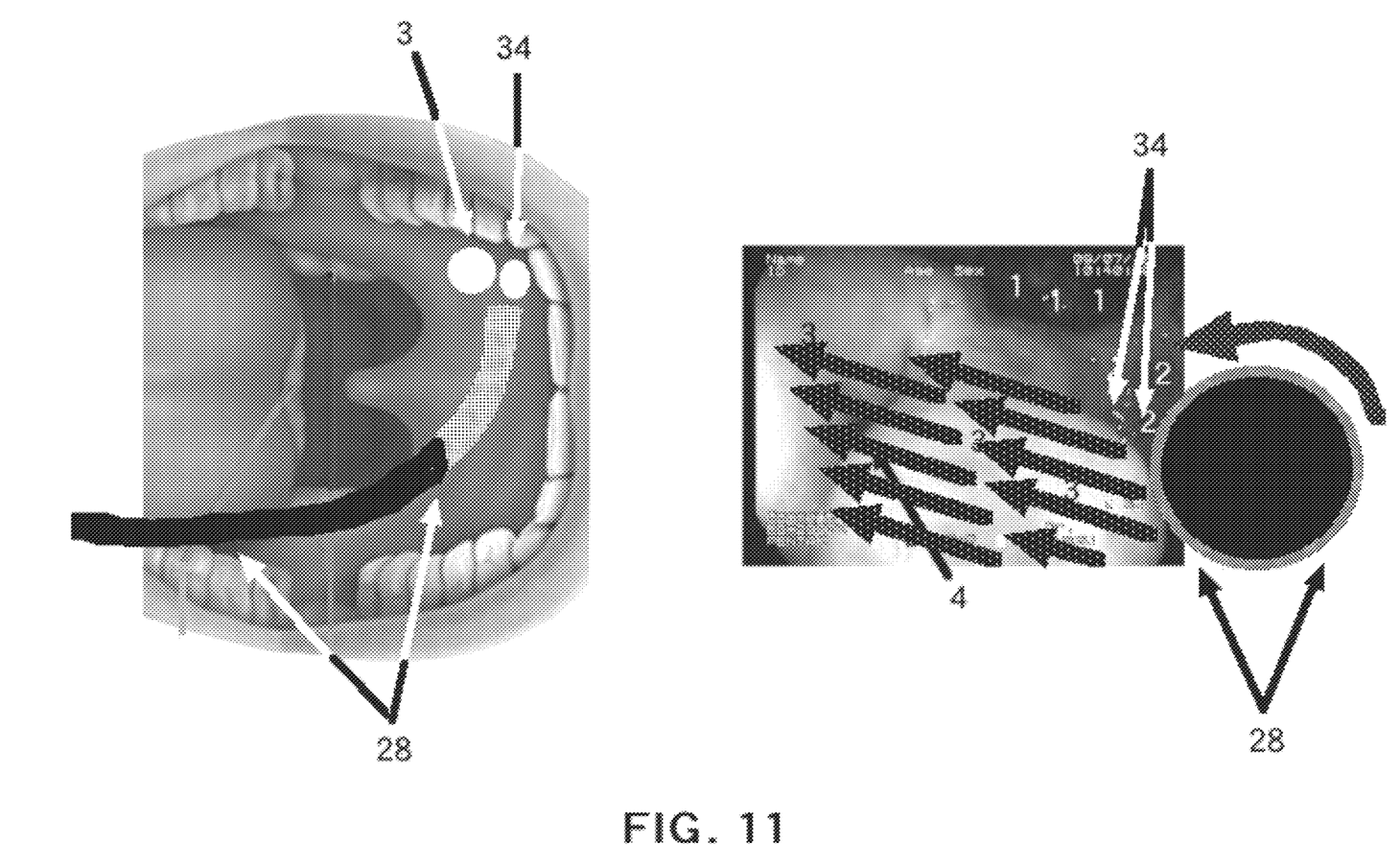
FIG. 11 is an image showing the state of retracting the right torus tubarius and inserting the flexible endoscope into the right Rosenmüller's fossa.

When the sedative drug is not effective, since muscles of the nasopharynx are contracted, the Rosenmüller's fossa becomes hollow, or the orifice of the Rosenmüller's fossa and the Rosenmüller's fossa become slit-like, and examination of the Rosenmüller's fossa is difficult.

Example 5

Flexible endoscope insertion method into the right tonsillar fossa (FIG. 9): the patient is placed in the left lateral position. The gastroscope is inserted through the mouth into the oropharynx, and the gastroscope is rotated to the right so as to be observed the palatine uvula in the direction of 12 o'clock for positioning the gastroscope on the lateral side of the tongue, and the gastroscope is gradually rotated to the left while maintaining a slight distance between the gastroscope and the right posterior palatine arch for medially retracting the tongue with the gastroscope itself, and the gastroscope is inserted into the right tonsillar fossa by slightly pushing the gastroscope, and the right tonsillar fossa is examined.

Figure 9:
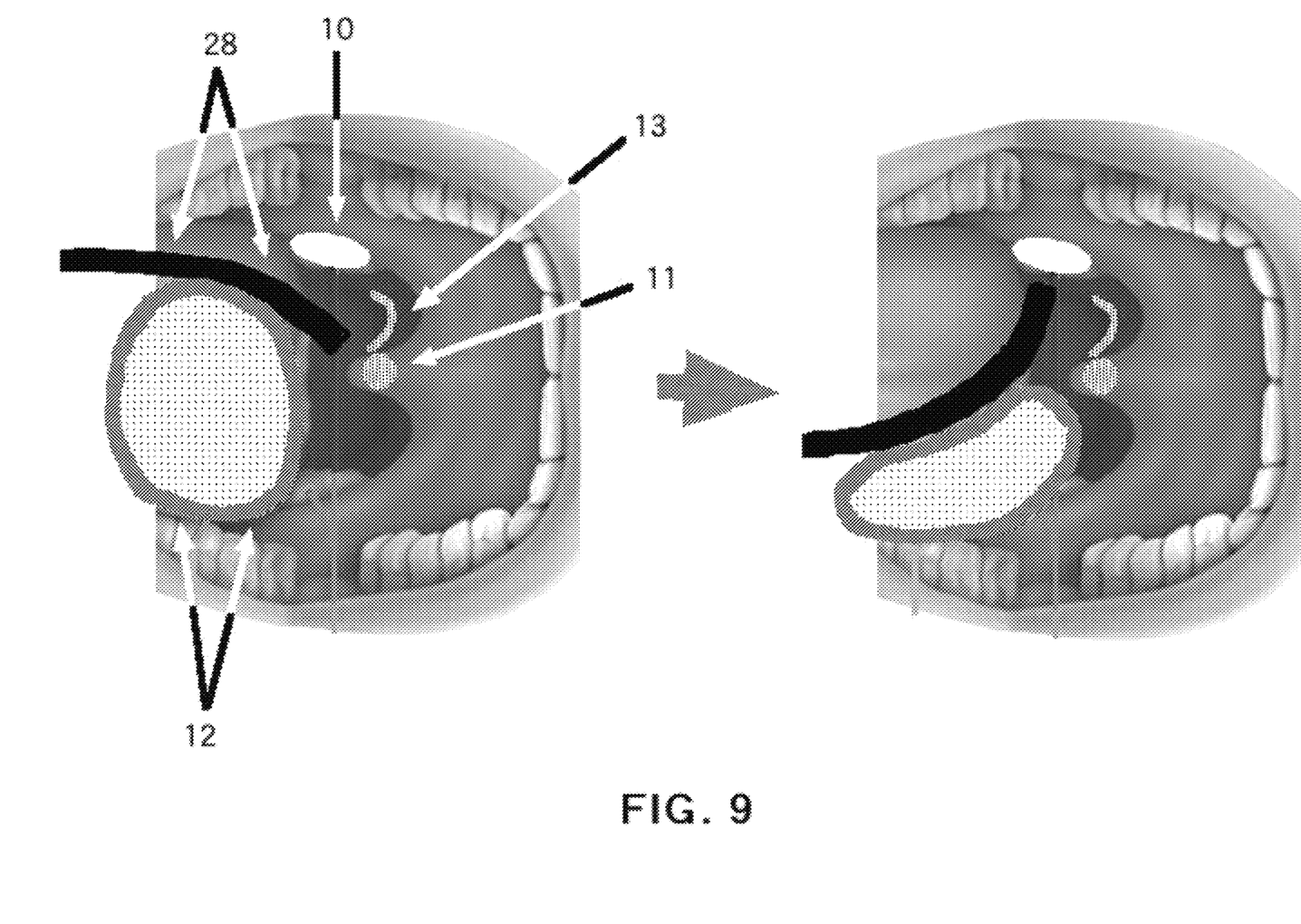
FIG. 9 is an image showing retracting the tongue and turning the tip of the flexible endoscope to the right tonsillar fossa.

If the tongue cannot be retracted medially, the tongue can be retracted medially by repeatedly rotating the gastroscope to the right or left until the fold becomes observable between the tongue and palatine tonsil.

Further, the gastroscope is inserted into the behind area of the right anterior palatine arch by slightly pushing the gastroscope, and the behind area of the right anterior palatine arch is examined.

When the muscles of the tongue are relaxed by using the sedative drug, the tongue retraction is easy.

Example 6

Flexible endoscope insertion method into the left lateral palatine region, the left maxillary linguogingival region and the incisive papilla region 32 (FIG. 10): the patient is placed in the left lateral position. The gastroscope 28 is inserted through the mouth into the oral cavity, and the gastroscope is rotated to the left so as to be observed the median palatine suture 29 in the direction of 6 o'clock, and the tip of the gastroscope is turned to the left lateral palatine region 31 and the left maxillary linguogingival region 30 by rotating the gastroscope further to the left, and the gastroscope is inserted into the left lateral palatine region and the left maxillary linguogingival region by slightly pushing the gastroscope, and the left lateral palatine region and the left maxillary linguogingival region are examined.

Figure 10:
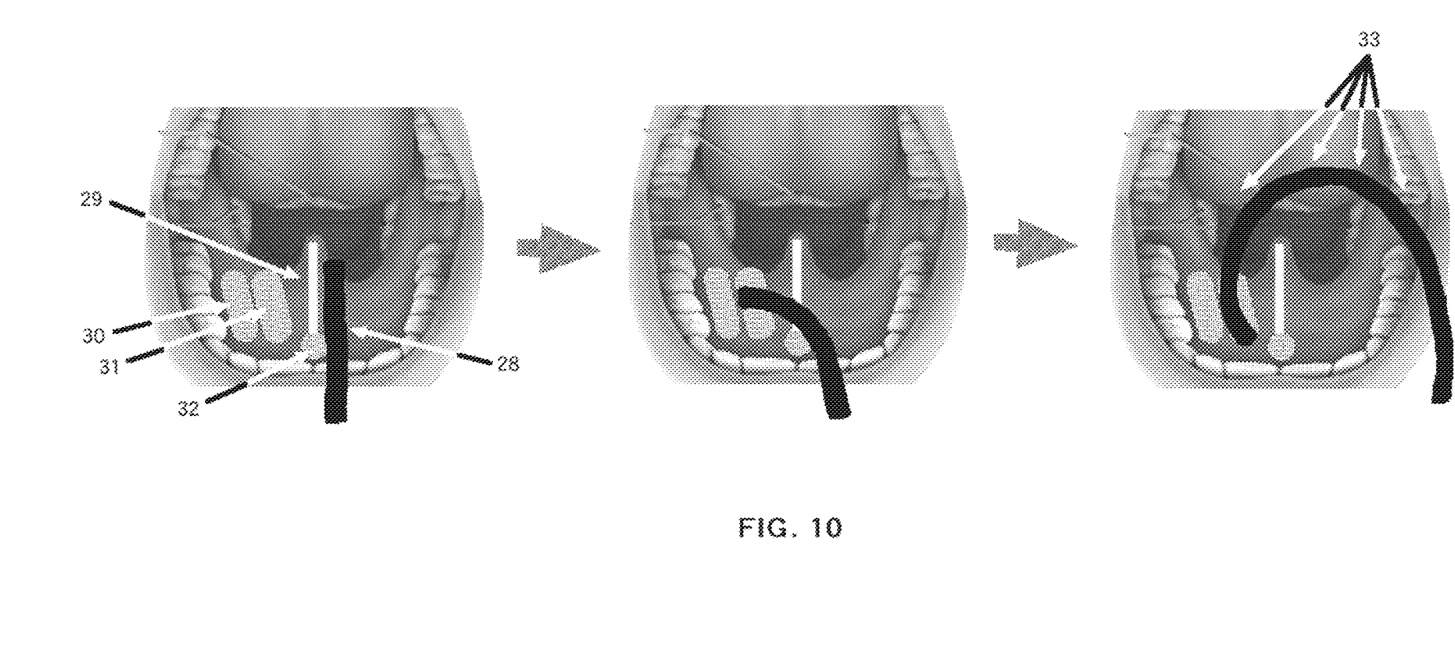
FIG. 10 is an image showing observing a lateral palatine region, a maxillary linguogingival region and a incisive papilla region by rotating the flexible endoscope by 360 degrees.

And the tip of the gastroscope is turned to the incisive papilla region by rotating the gastroscope further to the left, and the gastroscope is inserted into the incisive papilla region by slightly pushing the gastroscope, and the incisive papilla region is examined.

Example 7

Flexible endoscope insertion method into the right tympanic cavity and the right mastoid antrum: the patient is placed in the left lateral position. The flexible endoscope is inserted through the mouth into the oropharynx, and the flexible endoscope is inserted into the nasopharynx by gradually rotating the flexible endoscope to the right and simultaneously gradually applying an upward angle while maintaining a slight distance between the flexible endoscope and the posterior pharyngeal wall and slightly pushing the flexible endoscope. In the nasopharynx, the tip of the flexible endoscope is turned to the pharyngeal orifice of the right Eustachian tube by rotating the flexible endoscope to the left, and the right Eustachian tube is dilated by using a balloon catheter, drill, and laser catheter, and the flexible endoscope is inserted into the right Eustachian tube and right tympanic cavity by pushing the flexible endoscope, and the right Eustachian tube and right tympanic cavity is examined, and the aditus to the right mastoid antrum is dilated by using a balloon catheter, drill, and laser catheter, and the flexible endoscope is inserted into the right mastoid antrum by pushing the flexible endoscope, and the right mastoid antrum is examined.

Example 8

Flexible endoscope insertion method into the craniopharyngeal canal: the patient is placed in the left lateral position. The flexible endoscope is inserted through the mouth into the nasopharynx, and the nasopharyngeal wall around the nasopharyngeal orifice of the craniopharyngeal canal is incised, and the nasopharyngeal orifice of the craniopharyngeal canal is exposed, and the flexible endoscope is inserted into the craniopharyngeal canal by pushing the flexible endoscope, and the craniopharyngeal canal is examined Example 9

Flexible endoscope insertion method into the right maxillary sinus: the patient is placed in the left lateral position. The flexible endoscope is inserted through the mouth into the oropharynx, nasopharynx, and the right nasal cavity, and the right nasal cavity is examined, and the right maxillary sinus ostium is observed from the front, and the right maxillary sinus ostium is dilated by using a balloon catheter, drill, and laser catheter, and the flexible endoscope is inserted into the right maxillary sinus by pushing the flexible endoscope, and the right maxillary sinus is examined.

Example 10

Flexible endoscope insertion method into the right anterior ethmoidal sinus: the patient is placed in the left lateral position. The flexible endoscope is inserted through the mouth into the oropharynx, nasopharynx, and the right nasal cavity, and the right nasal cavity is examined, and the right anterior ethmoidal sinus ostium is observed from the front, and the right anterior ethmoidal sinus ostium is dilated by using a balloon catheter, drill, and laser catheter, and the flexible endoscope is inserted into the right anterior ethmoidal sinus by pushing the flexible endoscope, and the right anterior ethmoidal sinus is examined.

Example 11

Flexible endoscope insertion method into the right frontal sinus: the patient is placed in the left lateral position. The flexible endoscope is inserted through the mouth into the oropharynx, nasopharynx, and the right nasal cavity, and the right nasal cavity is examined, and the right frontal sinus ostium is observed from the front, and the right frontal sinus ostium is dilated by using a balloon catheter, drill, and laser catheter, and the flexible endoscope is inserted into the right frontal sinus by pushing the flexible endoscope, and the right frontal sinus is examined.

Example 12

Flexible endoscope insertion method into the right nasolacrimal duct and right lachrymal sac: the patient is placed in the left lateral position. The flexible endoscope is inserted through the mouth into the oropharynx, nasopharynx, and the right nasal cavity, and the right nasal cavity is examined, and the right nasolacrimal duct ostium is dilated by using a balloon catheter, drill, and laser catheter, and the flexible endoscope is inserted into the right nasolacrimal duct and right lachrymal sac by pushing the flexible endoscope, and the right nasolacrimal duct and right lachrymal sac is examined.

Example 13

Flexible endoscope insertion method into the right sphenoidal sinus: the patient is placed in the left lateral position. The flexible endoscope is inserted through the mouth into the oropharynx, nasopharynx, and the right nasal cavity, and the right nasal cavity is examined, and a loop of the flexible endoscope is made by applying a nasal plug and pushing the flexible endoscope, and the right sphenoidal sinus ostium is observed from the front, and the right sphenoidal sinus ostium is dilated by using a balloon catheter, drill, and laser catheter, and the flexible endoscope is inserted into the right sphenoidal sinus by pushing the flexible endoscope, and the right sphenoidal sinus is examined.

Example 14

Flexible endoscope insertion method into the right posterior ethmoidal sinus: the patient is placed in the left lateral position. The flexible endoscope is inserted through the mouth into the oropharynx, nasopharynx, and the right nasal cavity, and the right nasal cavity is examined, and a loop of the flexible endoscope is made by applying a nasal plug and pushing the flexible endoscope, or the loop of the flexible endoscope is not made, and the right posterior ethmoidal sinus ostium is observed from the front, and the right posterior ethmoidal sinus ostium is dilated by using a balloon catheter, drill, and laser catheter, and the flexible endoscope is inserted into the right posterior ethmoidal sinus by pushing the flexible endoscope, and the right posterior ethmoidal sinus is examined.

Example 15

Flexible endoscope insertion method into the anterior nasopharyngeal wall: the patient is placed in the left lateral position. The flexible endoscope is inserted through the mouth into the oropharynx, nasopharynx, and the right nasal cavity, and the right nasal cavity is examined, and a loop of the flexible endoscope is made by applying a nasal plug and pushing the flexible endoscope, and the flexible endoscope is re-inserted into the nasopharynx by pushing the flexible endoscope, and the anterior nasopharyngeal wall is observed from the front, and the anterior nasopharyngeal wall is examined.

Example 16

Figure 7:
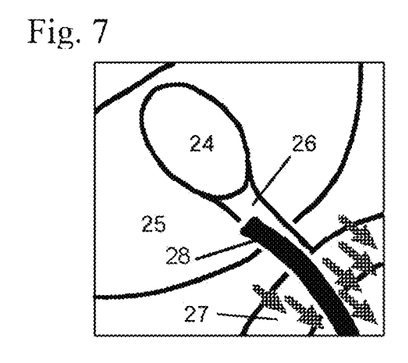
FIG. 7 is an image showing the state of retracting the duodenum, transverse colon, and greater omentum and stretching the right lateral side of the common bile duct.

Natural orifice transluminal cholecystectomy: the flexible endoscope is inserted through the anus into the large intestine, and the device is projected from the flexible endoscope, and the wall of the large intestine is incised, and the flexible endoscope is inserted into the abdominal cavity. Then, the flexible endoscope is inserted around the common bile duct, and the tip of the flexible endoscope is turned to the right lateral side of the common bile duct by rotating the flexible endoscope to the left, and simultaneously the duodenum, transverse colon, and greater omentum are medially and inferiorly retracted with the flexible endoscope itself by rotating the flexible endoscope to the left for securing the broader operative field (flexible endoscopic duodeno-colono-omental retraction method) (FIG. 7). Then, the cystic duct and cystic artery are exposed in the right lateral side of the distended common bile duct, and the cystic duct and cystic artery are ligated and incised, and the gallbladder is resected.

Example 17

Single-incision flexible endoscopic cholecystectomy: the abdominal wall is incised, and a port is established in the abdominal incision, and the flexible endoscope is inserted through the port into the abdominal cavity. Then, the flexible endoscope is inserted around the common bile duct, and the tip of the flexible endoscope is turned to the right lateral side of the common bile duct by rotating the flexible endoscope to the left, and simultaneously the duodenum, transverse colon, and greater omentum are medially and inferiorly retracted with the flexible endoscope itself by rotating the flexible endoscope to the left for securing the broader operative field (flexible endoscopic duodeno-colono-omental retraction method) (FIG. 7). Then, the cystic duct and cystic artery are exposed in the right lateral side of the distended common bile duct, and the cystic duct and cystic artery are ligated and incised, and the gallbladder is resected.

DESCRIPTION OF THE REFERENCE NUMERALS

1. Nasal cavity
2. Superior nasopharyngeal wall
3. Right torus tubarius
4. Pharyngeal orifice of the right Eustachian tube
5. Roof of the right nasal cavity
6. Right nasal cavity
7. Nasal septum
8. Roof of the left nasal cavity
9. Left nasal cavity
10. Right tonsillar fossa
11. Palatine uvula
12. Tongue
13. Right posterior palatine arch
14. Right anterior palatine arch
15. Right frontal sinus
16. Right anterior ethmoidal sinus ostium
17. Right maxillary sinus ostium
18. Right posterior ethmoidal sinus ostium
19. Right nasolacrimal duct ostium
20. Right sphenoidal sinus
21. Nasal plug
22. Right tympanic membrane
23. Left nasolacrimal duct ostium
24. Gall bladder
25. Liver
26. Common bile duct
27. Duodenum
28. Flexible endoscope
29. Median palatine suture
30. Maxillary linguogingival region
31. Lateral palatine region
32. Incisive papilla region
33. Looping of the flexible endoscope
34. Right Rosenmüller's fossa

The invention claimed is:

1. A flexible endoscope insertion method, comprising:
   (a) rotating a hollow organ by 45 to 90 degrees by changing a body position to a semilateral position or a lateral position for observing a lateral wall of a lumen of the hollow organ, wherein the body position was a supine, semi-recumbent, sitting, lithotripsy, or prone position;
   (b) turning a tip of the flexible endoscope to the lateral wall of the lumen by rotating an insertion portion of the flexible endoscope counterclockwise or clockwise from a perspective of a person operating the endoscope;
   inserting the flexible endoscope into a lumen while rotating the flexible endoscope clockwise or counterclockwise;
   turning the tip of the flexible endoscope to the lateral wall of the lumen by rotating the flexible endoscope counterclockwise after inserting the flexible endoscope while rotating the flexible endoscope clockwise, or clockwise after inserting the flexible endoscope while rotating the flexible endoscope counterclockwise; and examining the lateral wall of the lumen; and
   (c) retracting the hollow organ with the flexible endoscope itself by rotating the insertion portion of the flexible endoscope counterclockwise or clockwise from the perspective of the person operating the endoscope for securing a visual field.

2. The flexible endoscope insertion method according to claim 1, comprising the steps of:
   placing the patient in a left lateral position;
   inserting the flexible endoscope into a nasopharynx while rotating the flexible endoscope clockwise;
   turning the tip of the flexible endoscope to the right lateral wall of the nasopharynx by rotating the flexible endoscope counterclockwise; and
   examining a pharyngeal orifice of a right Eustachian tube.

3. The flexible endoscope insertion method according to claim 1,
   wherein (b) comprises turning the tip of the flexible endoscope by rotating the flexible endoscope by 360 degrees counterclockwise or clockwise, such that the flexible endoscope forms a loop.

4. The flexible endoscope insertion method according to claim 3,
   wherein the pharyngeal orifice of the right Eustachian tube can be observed by rotating the flexible endoscope by 360 degrees counterclockwise in an oropharynx and nasopharynx, such that the flexible endoscope forms a loop.

5. The flexible endoscope insertion method according to claim 4, comprising the steps of:
   placing the patient in a left lateral position;
   inserting the flexible endoscope into the oropharynx;
   turning the tip of the flexible endoscope by rotating the flexible endoscope by 90 degrees counterclockwise;
   furthermore turning the tip of the flexible endoscope by rotating the flexible endoscope counterclockwise by 180 degrees;
   inserting the flexible endoscope into a nasopharynx while rotating the flexible endoscope counterclockwise by 90 degrees; and directing the tip of the flexible endoscope to the right lateral wall of the nasopharynx; examining the pharyngeal orifice of the right Eustachian tube.

6. The flexible endoscope insertion method according to claim 1,
wherein the flexible endoscope is transorally inserted into a nasopharynx, a Rosenmüller's fossa, a persistent craniopharyngeal canal, an Eustachian tube, a tympanic cavity, a mastoid antrum, a nasal cavity, a maxillary sinus, a frontal sinus, a sphenoidal sinus, an ethmoidal sinus, a nasolacrimal duct, or a lachrymal sac.

7. The flexible endoscope insertion method according to claim 6, comprising the steps of:
placing the patient in a left lateral position;
inserting the flexible endoscope into the nasopharynx while rotating the flexible endoscope clockwise; and
inserting the flexible endoscope into the nasal cavity.

8. The flexible endoscope insertion method according to claim 6, comprising the steps of:
placing the patient in a right lateral position;
inserting the flexible endoscope into the nasopharynx while rotating the flexible endoscope counterclockwise; and
inserting the flexible endoscope into the nasal cavity.

9. The flexible endoscope insertion method according to claim 1,
further comprising observing a tonsillar fossa by medially retracting a tongue with the flexible endoscope itself.

10. The flexible endoscope insertion method according to claim 9, comprising the steps of:
placing the patient in the left lateral position;
inserting the flexible endoscope through a mouth into a oropharynx;
rotating the flexible endoscope clockwise so as to observe a palatine uvula in the 12 o'clock position with respect to a field of view of the endoscope for positioning the flexible endoscope on the lateral side of the tongue;
rotating the flexible endoscope counterclockwise while maintaining a distance between the flexible endoscope and a right posterior palatine arch for medially retracting the tongue with the flexible endoscope itself;
inserting the flexible endoscope into a right tonsillar fossa by pushing the flexible endoscope; and
examining the right tonsillar fossa.

11. The flexible endoscope insertion method according to claim 1,
further comprising observing a lateral palatine region, a maxillary linguogingival region and an incisive papilla region by rotating the flexible endoscope by 360 degrees counterclockwise or clockwise in an oral cavity, wherein the flexible endoscope forms a loop in the oral cavity.

12. The flexible endoscope insertion method according to claim 11, comprising the steps of:
placing the patient in a left lateral position;
inserting the flexible endoscope through the mouth into an oral cavity;
rotating the flexible endoscope counterclockwise by 180 degrees so as to be observed a median palatine suture in a 6 o'clock position with respect to a field of view of the endoscope;
turning the tip of the flexible endoscope to a left lateral palatine region and a left maxillary linguogingival region by rotating the flexible endoscope counterclockwise by 90 degrees;
examining the left lateral palatine region and the left maxillary linguogingival region;
turning the tip of the flexible endoscope to an incisive papilla region by rotating the flexible endoscope counterclockwise by 90 degrees; and
examining the incisive papilla region.

13. The flexible endoscope insertion method according to claim 1,
wherein the flexible endoscope is inserted into a hypopharynx, larynx, trachea, bronchus, bile duct, pancreatic duct, duodenum, stomach, esophagus, urethra, bladder, ureter, renal pelvis, vagina, uterus, or fallopian tube.

14. The flexible endoscope insertion method according to claim 1,
further comprising observing a Rosenmüller's fossa by laterally retracting a torus tubarius with the flexible endoscope itself.

15. The flexible endoscope insertion method according to claim 14, comprising the steps of:
placing the patient in a left semilateral position;
inserting the flexible endoscope through the mouth into a oropharynx;
inserting the flexible endoscope into a nasopharynx while rotating the flexible endoscope clockwise;
turning the tip of the flexible endoscope to a right Rosenmüller's fossa ostium medial to a right torus tubarius by rotating the flexible endoscope counterclockwise;
inserting the flexible endoscope into the right Rosenmüller's fossa while counterclockwise rotating the flexible endoscope for laterally retracting the right torus tubarius with the flexible endoscope itself; and
examining the right Rosenmüller's fossa.

* * * * *